(12) United States Patent
Enzinna et al.

(10) Patent No.: US 11,908,305 B2
(45) Date of Patent: Feb. 20, 2024

(54) NURSE CALL PILLOW SPEAKER WITH AUDIO EVENT DETECTION AND METHODS FOR SAME

(71) Applicant: Curbell Medical Products, Inc., Orchard Park, NY (US)

(72) Inventors: Donald J. Enzinna, Lockport, NY (US); Daniel J. MacDonald, East Amherst, NY (US); Edward Wilkolaski, South Wales, NY (US)

(73) Assignee: Curbell Medical Products, Inc., Orchard Park, NY (US)

( * ) Notice: Subject to any disclaimer, the term of this patent is extended or adjusted under 35 U.S.C. 154(b) by 0 days.

(21) Appl. No.: 15/922,562

(22) Filed: Mar. 15, 2018

(65) Prior Publication Data

US 2019/0287381 A1  Sep. 19, 2019

(51) Int. Cl.
| | | |
|---|---|---|
| G05B 23/02 | (2006.01) | |
| G08B 25/01 | (2006.01) | |
| G08B 5/22 | (2006.01) | |
| G08B 25/00 | (2006.01) | |
| A61B 5/11 | (2006.01) | |
| H04R 3/12 | (2006.01) | |
| G16H 40/60 | (2018.01) | |
| G08B 25/10 | (2006.01) | |

(52) U.S. Cl.
CPC .......... *G08B 25/014* (2013.01); *A61B 5/1115* (2013.01); *G08B 5/222* (2013.01); *G08B 25/009* (2013.01); *H04R 3/12* (2013.01); *G08B 25/016* (2013.01); *G08B 25/10* (2013.01); *G16H 40/60* (2018.01)

(58) Field of Classification Search
CPC .... G08B 25/014; G08B 5/222; G08B 25/009; G08B 25/016; G08B 25/10; A61B 5/1115; H04R 3/12; G16H 40/60
USPC ......................................................... 340/3.3
See application file for complete search history.

(56) References Cited

U.S. PATENT DOCUMENTS

| | | | | |
|---|---|---|---|---|
| 3,974,681 A | * | 8/1976 | Namery ............... | G01N 29/032 128/DIG. 3 |
| 5,694,467 A | * | 12/1997 | Young, III ............ | H04M 1/60 379/267 |
| 2003/0043302 A1 | * | 3/2003 | Stoner ................. | H04N 5/63 348/E5.103 |
| 2003/0216670 A1 | * | 11/2003 | Beggs ................. | A61B 5/6892 600/595 |
| 2005/0185799 A1 | * | 8/2005 | Bertram ............... | A61B 5/0002 381/67 |

(Continued)

FOREIGN PATENT DOCUMENTS

CA  2157405 C  * 10/2000  .......... G06F 19/323

*Primary Examiner* — Naomi J Small
(74) *Attorney, Agent, or Firm* — Hodgson Russ LLP

(57) ABSTRACT

The present disclosure may be embodied as a pillow speaker system. The pillow speaker system has a patient interface device (PID) having a processor and an audio output. A nurse call audio port is provided to communicate with a nurse call station. A detection circuit is provided to detect a nurse call signal and a provide nurse call indicator if a nurse call signal is present. The processor is programmed to receive the nurse call indicator from the detection circuit; provide a nurse call audio signal to the audio output if the nurse call indicator is received; and mute audio signals to the audio output except the nurse call audio signal.

30 Claims, 8 Drawing Sheets

(56) References Cited

U.S. PATENT DOCUMENTS

| | | | |
|---|---|---|---|
| 2006/0294554 A1* | 12/2006 | Hausman | H04N 7/17318 725/81 |
| 2008/0057858 A1* | 3/2008 | Smith | H04R 1/1033 455/3.05 |
| 2011/0037613 A1* | 2/2011 | Chakravorti | G01R 31/50 340/870.07 |
| 2013/0229583 A1* | 9/2013 | Kuciera | H04N 21/42222 348/734 |
| 2016/0048226 A1* | 2/2016 | Kuciera | G08C 19/16 345/173 |
| 2017/0061784 A1* | 3/2017 | Clough | G06F 3/04842 |
| 2017/0222829 A1* | 8/2017 | Kessler | H04L 12/40058 |
| 2018/0004384 A1* | 1/2018 | Fitzgerald | G06F 3/04817 |

* cited by examiner

NURSE CALL PILLOW SPEAKER WITH AUDIO EVENT DETECTION AND METHODS FOR SAME

FIELD OF THE DISCLOSURE

The present disclosure relates to a pillow speaker for use in a hospital environment, and more particularly, to the processing of audio signals transmitted and received by a digital pillow speaker system.

BACKGROUND OF THE DISCLOSURE

The typical pillow speaker contains a speaker which, in most cases, is wired directly to analog output circuits in the nurse call system patient station to which the pillow speaker is connected. The pillow speaker provides a conduit for the analog audio created in the nurse call system to be broadcast by the speaker in the pillow speaker. The nurse call system typically provides two different types of analog audio for broadcast at the pillow speaker; nurse call voice audio and entertainment audio. The selection of the appropriate analog audio source for broadcast at the speaker in the pillow speaker is performed by the nurse call system. In one state, the speaker in the pillow speaker is electrically connected to a microphone at a nursing station, allowing the nurse to speak to the patient through the system. When the nurse is not speaking with the patient, the nurse call system typically defaults to an electrical connection enabling analog audio signals from the in-room entertainment device, such as a television, to be broadcast at the speaker on the pillow speaker.

Similar circuits exists for microphones used in pillow speakers, when microphones is present. Analog audio generated by the pillow speaker user speaking into the microphone mounted in the pillow speaker is amplified by the nurse call system for broadcast at a nursing station, enabling a two-way dialog between patient and nurse.

FIG. 1 shows a typical circuit used to bring TV audio to a patient via a pillow speaker. During a nurse call event, the nurse may wish to communicate with the patient using the pillow speaker and alternately listen to a response by using the same speaker as a microphone. Audio from the television is supplied to the speaker through a 10 ohm resistor whereas nurse call audio is directly applied to the speaker terminals. Both the television and nurse call system share a common ground. Signal management is accomplished in a patient station which is mounted typically on a wall in proximity to the patient's bed. An active nurse call causes the TV to be muted and connects the speaker as a microphone to allow the patient to talk to the nurse. The nurse has a push-to-talk button or a voice-activated circuit to reverse the path and allow the nurse to speak to the patient. With this arrangement, there is no way to determine the direction of signal flow, from patient to nurse or from nurse to patient.

Incorporating a tablet or other such device in a patient-interface device (PID) of a pillow speaker creates an issue for prioritizing competing audio sources for broadcast over the pillow speaker system speaker or speakers. For example, the use of a tablet introduces an additional source of audio for consumption by the bed-bound patient—audio generated by the tablet itself from internal software or online sources. The existing scheme of relying on the nurse call system to select the audio for broadcast at the speakers in the pillow speaker is no longer valid, as there is no effective way to convey the use of tablet computer generated audio to the nurse call system or for the nurse call system to effectively control the behavior of the tablet computer.

Accordingly, there is a critical, long-felt need for a system able to prioritize nurse call signals over other signals.

BRIEF SUMMARY OF THE DISCLOSURE

In an aspect, the present disclosure may be embodied as a pillow speaker system. The pillow speaker system has a patient interface device (PID) having a processor and an audio output. A nurse call audio port is provided to communicate with a nurse call station. A detection circuit is provided to detect a nurse call signal and provide a nurse call indicator if a nurse call signal is present. The processor is programmed to receive the nurse call indicator from the detection circuit; provide a nurse call audio signal to the audio output if the nurse call indicator is received; and mute audio signals to the audio output except the nurse call audio signal. The pillow speaker system may further include an impedance matching network in communication with the nurse audio port.

In some embodiments, the detection circuit detects a nurse call signal by detecting an audio signal on the nurse call audio port. In other embodiments, the detection circuit detects a nurse call signal by detecting a nurse call indication signal. The detection circuit may de-assert the nurse call indicator if a nurse call signal is not detected for a predetermined period of time. The processor may be further programmed to unmute audio signals if the nurse call indicator is de-asserted. The detection circuit may be, for example, an envelope detector circuit.

The pillow speaker system may have a hub in digital communication with the PID. The nurse call audio port may be in analog communication with the hub. The hub digitizes the nurse call audio signal to send a digital nurse call audio signal to the PID. For example, the hub and the PID may communicate via a digital port which may be a universal serial bus (USB) port. The hub may further include the detection circuit, and the nurse call indicator is provided to the PID as a digital signal.

The PID may include a microphone. In such embodiments, the PID is further programmed to provide a microphone signal from the microphone to the nurse call audio port if a nurse call indicator is received. The pillow speaker system may include a conditioner for conditioning the microphone signal. The conditioner may be an attenuator for attenuating the microphone signal. The attenuator is a software module programmed in the processor. In other embodiments, the attenuator is a discrete electrical circuit. Other attenuators are known and are within the scope of the present disclosure. The conditioner may also be a filter or amplifier.

In some embodiments, the pillow speaker system includes an entertainment audio port in analog communication with the hub. Such an entertainment audio port may be connected to a television, a video game system, a handheld system, or other devices. The hub digitizes an entertainment audio signal of the entertainment audio line to send a digital entertainment audio signal to the PID.

In another aspect, the present disclosure may be embodied as a method of providing a nurse call audio signal to a digital pillow speaker. A nurse call signal is detected and a nurse call indicator is asserted for the digital pillow speaker if a nurse call signal is detected. A nurse call audio signal at a nurse call audio port is digitized and transmitted to the digital pillow speaker. A digital nurse call microphone signal is received from the digital pillow speaker. The received digital nurse call microphone signal is transmitted as an analog microphone signal on the nurse call audio port. The method may further include attenuating the analog microphone signal to match a microphone signal of a nurse call system.

In another aspect, the present disclosure may be embodied as a method of prioritizing audio signals in a digital pillow speaker. An audio signal is provided to an audio output of the digital pillow speaker. A nurse call indicator is received from a digital port of the digital pillow speaker and the audio signal is muted. A digital nurse call audio signal is received from the digital port. The received digital nurse call audio signal is converted to an analog nurse call audio signal and provided to an audio output. The method may further include receiving a microphone signal from a microphone of the digital pillow speaker, and digitizing the microphone signal to provide a digital microphone signal to the digital port.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Figure 1:
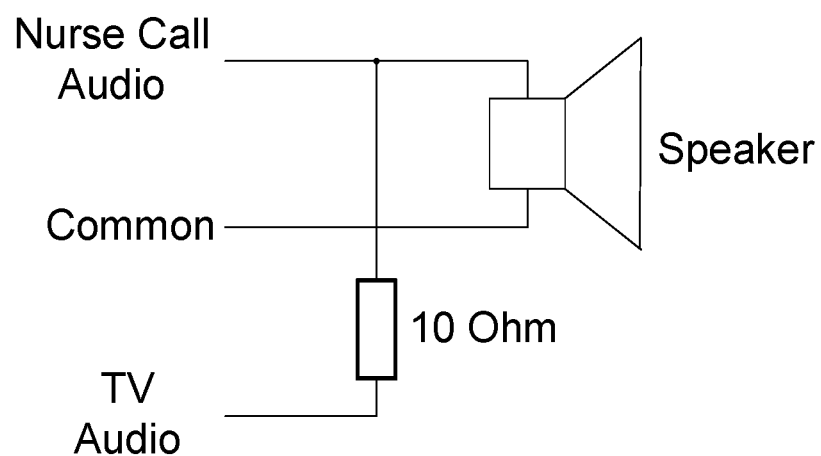
FIG. 1 is a partial schematic of a prior art pillow speaker system.
Figure 2:
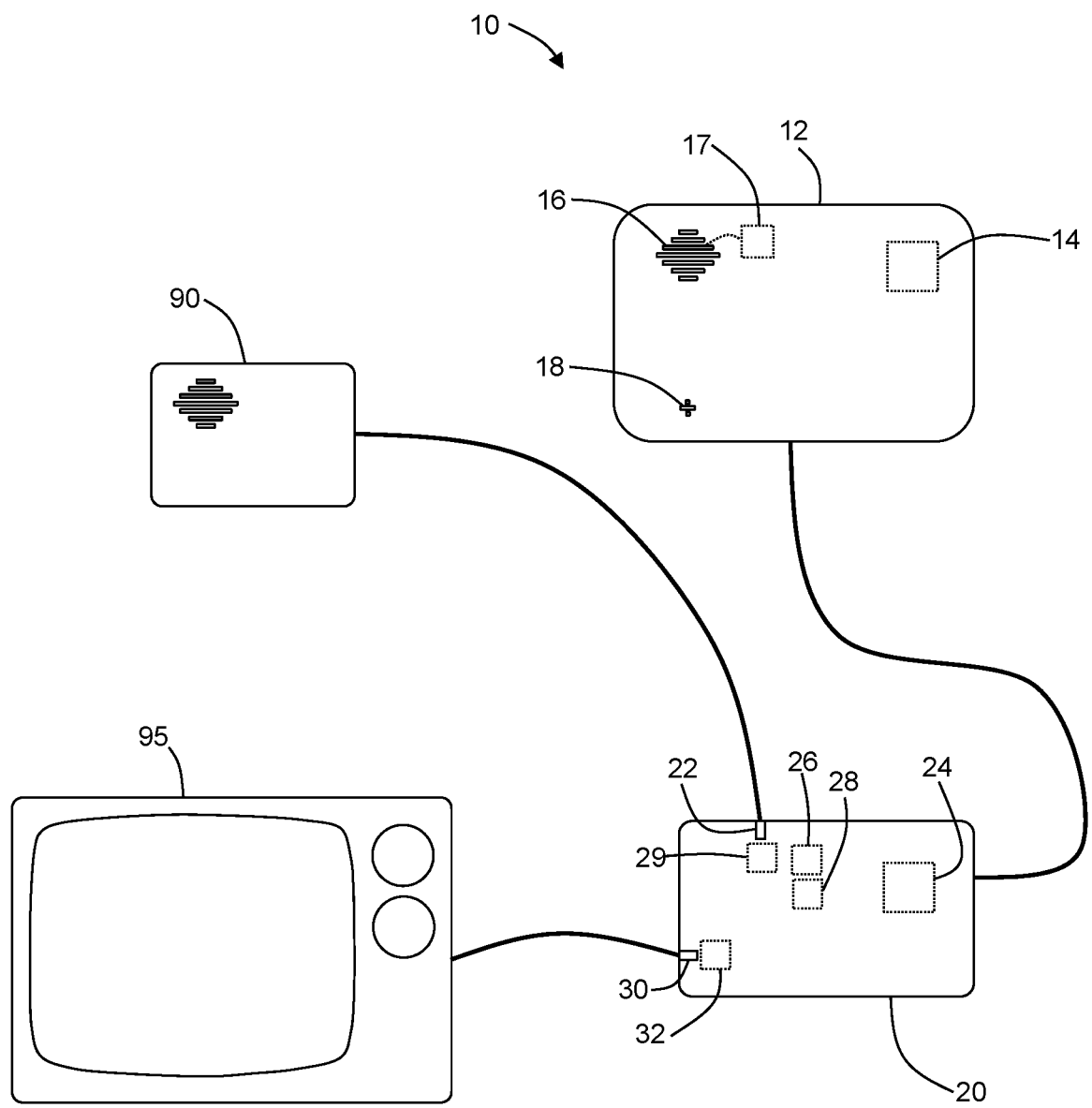
FIG. 2 is a block diagram of a pillow speaker system according to an embodiment of the present disclosure.

In an aspect of the present disclosure, a pillow speaker system 10 is provided (see, e.g., FIG. 2). The pillow speaker system comprises a patient interface device (PID) 12 which may be, for example, a tablet computer, smartphone, or any other device which allows the patient to interact with the pillow speaker system. The PID 12 includes a processor 14 and an audio output 16. The audio output 16 of the PID 12 is an analog output suitable for connection to, for example, a speaker and/or a headphone jack (represented in FIG. 2 as a speaker grille).

The pillow speaker system 10 includes a nurse call audio port 22. In some embodiments, the pillow speaker system 10 includes a hub 20 which is in communication with the nurse call audio port 22. For example, the hub 20 may house the nurse call audio port 22. In such embodiments, the hub 20 is in digital communication with the PID 12. For example, the hub 20 and PID 12 may be connected by way of a universal serial bus (USB) connection. The nurse call audio port 22 is a port configured for communication with a nurse call station 90. As described above, nurse call stations 90 are known in the art and generally communicate by providing an analog nurse call audio signal. As such, the nurse call audio port 22 may be an analog port for connection to such a nurse call station 90 and may receive a nurse call audio signal from the nurse call station 90. The nurse call audio port 22 may comprise a single bidirectional audio connection, two unidirectional audio connections, or any other configuration and combinations suitable for communicating with a nurse call station 90.

The pillow speaker system 10 further comprises a detection circuit 24 for detecting a nurse call signal. If a nurse call signal is present (is detected by the detection circuit 24), the detection circuit 24 provides a nurse call indicator. For example, the detection circuit 24 may provide a nurse call indicator to the PID 12. In some embodiments, the detection circuit 24 may be a part of the hub 20 and the nurse call indicator may be provided to the PID 12 as a digital signal. In some embodiments, the detection circuit 24 detects a nurse call signal by monitoring the nurse call audio port for a nurse call audio signal. In such embodiments, the detection circuit 24 may be, for example, an envelope detector. For example, an envelope detector may comprise two capacitors and two diodes to output a low frequency signal corresponding to individual peaks of the detected nurse call audio signal. A typical frequency range of the nurse call audio signal is 300-3500 Hz, and the frequency range of a suitable envelope detector may be in the sub-Hertz frequency range (i.e., less than 1 Hz). In this way, a typical burst of audio from a spoken word will quickly charge up the detector circuit, and the detection circuit will stay charged for a predetermined period of time (e.g., few seconds). The nurse call indicator can be provided by, for example, a comparator which provides a signal corresponding to an asserted nurse call indicator if an output of the envelope detector exceeds a threshold value. In the absence of further audio signals on the nurse call audio port, the detection circuit will discharge after this period, thereby de-asserting the nurse call indicator. In some embodiments, a delay may be introduced, for example, by a microprocessor, if the detection circuit discharges too quickly.

In other embodiments, a nurse call system 90 may provide a nurse call indication signal—i.e., a signal separate from the audio signal(s) of the dialog—to indicate that a dialog is active (or should be activated) between the nurse and the patient. In such embodiments, the detection circuit 24 may be configured to detect the nurse call indication signal and assert the nurse call indicator if the nurse call indication signal is present (and, for example, de-asserting the nurse call indicator when the indication signal is no longer present). For example, the nurse call indication signal may be a control signal for a light (a "talkback light") which illuminates when a dialog is active between a nurse and a patient. Other indication signals may indicate the start of a dialog between the patient and a nurse—for example, providing a tone or a beep to alert the patient that the nurse is calling. In such examples, a combination of the above-described detection circuits may be used to detect the tone indicating the start of a dialog and to detect audio signals to indicate the continuation of the dialog. Other detection circuits will be apparent to one skilled in the art in light of the present disclosure and are considered within the scope of the present disclosure. For example, the detection circuit may use a timer to de-assert the nurse call signal flag.

The processor 14 of the PID 12 is programmed to receive the nurse call indicator provided by the detection circuit 24. The processor 14 will provide a nurse call audio signal to the audio output 16 of the PID 12 if the nurse call indicator is received. For example, the processor 14 may receive the digital nurse call audio signal from the hub 20 and provide the digital signal to a digital-to-analog converter (DAC) 17 in communication with the audio output 16. The processor 14 will mute audio signals to the audio output 16 except the nurse call audio signal. For example, if entertainment audio is being provided to the audio output 16, the entertainment audio will be muted in favor of the nurse call audio signal. By "muted" it is to be understood that other audio signals are attenuated, and, in some cases, attenuated so as to be reduced to zero (i.e., silenced).

The PID 12 may include a microphone 18. In such embodiments, the processor 14 may be further programmed to provide a microphone signal received from the microphone to the nurse call audio port 22 if the nurse call indicator is received. For example, in embodiments wherein the nurse call audio port 22 is in communication with (including housed within) a hub 20, the PID 12 may digitize the microphone signal and send the digital microphone signal to the hub 20 which may, in turn, convert the digital microphone signal to an analog microphone signal to the nurse call audio port 22.

The pillow speaker system 10 may include a conditioner for conditioning the microphone signal. The conditioner 26 may by comprise an attenuator for attenuating the microphone signal. An attenuator may be required in some embodiments in order to match a line level audio coming from the PID to a millivolt level signal typical for some microphone outputs (and expected by some nurse call stations 90). Similarly, the pillow speaker system 10 may comprise an amplifier 28 for amplifying a nurse call audio signal received at the nurse call audio port 22. Levels to and from the nurse call audio port 22 may be on the order of hundreds of millivolts and may require the use of an amplifier 28 and/or conditioner 26. Because a microphone signal may be indicative of a continuing nurse call dialog, the detection circuit 24 may receive a summed signal comprising a nurse call audio signal (i.e., from the nurse call station 90) and the microphone signal (i.e., from the PID 12) to determine whether or not to continue assert/continue asserting the nurse call indicator. The pillow speaker system 10 may further comprise a nurse call impedance matching network 29 to provide a compatible load impedance to the nurse call station 90. The conditioner may also be a filter or amplifier.

The pillow speaker system 10 may further comprise an entertainment audio port 30 for receiving an entertainment audio signal. For example, the hub 20 may comprise an entertainment audio port 30 for receive an entertainment audio signal from an entertainment device 95 (e.g., a television) located in the room of the patient. The hub 20 may digitize an entertainment audio signal of the entertainment audio line to send a digital entertainment audio signal to the PID 12. The PID 12 may provide the received entertainment audio signal to the audio output 16. The entertainment audio signal is an example of an audio signal which may be muted in favor of a nurse call audio signal when the nurse call indicator is asserted. The pillow speaker system 10 may further comprise an impedance matching network 32 in communication with the entertainment audio port 30 for providing a compatible load impedance to a connected entertainment device 95.

Figure 3:
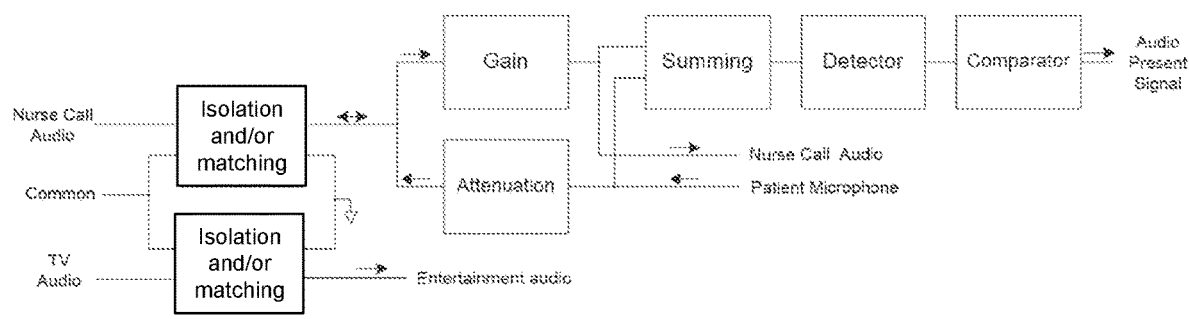
FIG. 3 is a diagram of a nurse call system pillow speaker with an integrated tablet computer according to an embodiment of the present disclosure; electrical connection diagram for an embodiment of present disclosure, showing electrical connections between the nurse call station, hub, and a patient interaction device.

With reference to FIG. 3, in an example of detection circuit 24, the detection circuit 24 may operate by first receiving the summed optionally weighted voltages of the nurse call audio signal and the patient microphone audio signal. Detection circuit 24 may then rectify the summed waveform to detect its envelope. A comparator circuit may then compare the envelope's voltage to a reference voltage and drive an output stage when the envelope's voltage is greater than the reference voltage. The output stage may be configured to set a nurse call indicator. The output stage may be an open-collector transistor, an open-drain transistor with a pull-up resistor, or any other suitable design. Prior to the summing stage, either or both of the nurse call audio signal and the patient microphone signal may have passed through an impedance matching network or an isolation network. In some embodiments, the result of the detection circuit is a digital signal indicating a presence of a nurse call signal, and the detection circuit may be implemented in any fashion to produce such a digital signal.

Figure 4:
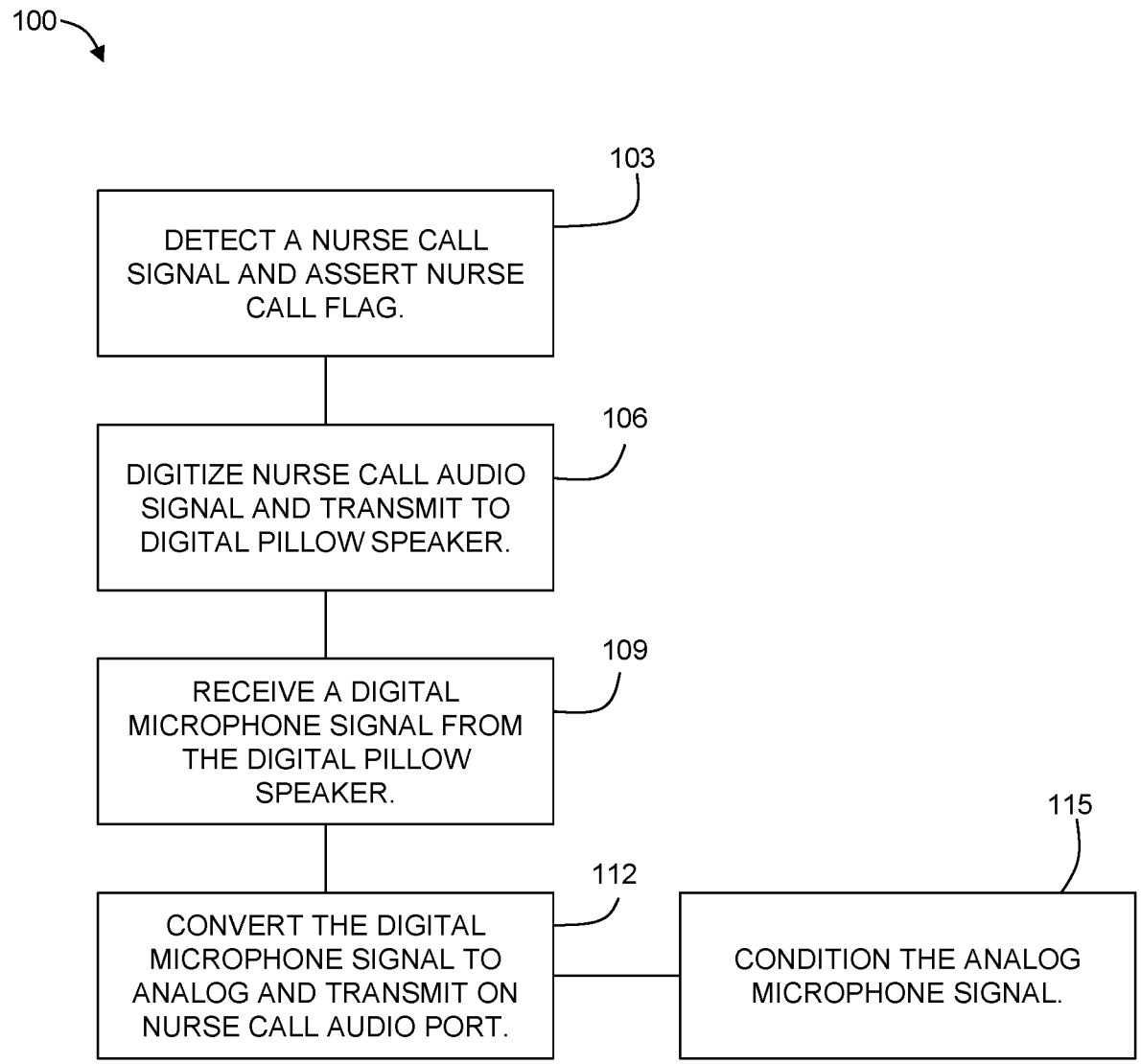
FIG. 4 is a method according to another embodiment of the present disclosure.

With reference to FIG. 4, in another aspect, the present disclosure may be embodied as a method 100 for providing a nurse call audio signal to a digital pillow speaker. Such a method 100 may be performed by a hub of a pillow speaker system if such a system includes a hub. In other pillow speaker systems, the method 100 may be performed by a PID. Yet other embodiments of pillow speaker systems may perform method 100 through one or more other components. The method 100 may include detecting 103 a nurse call signal and asserting a nurse call indicator of the digital pillow speaker if a nurse call signal is detected 103. A nurse call audio signal from a nurse call audio port is digitized 106 and the digitized 106 nurse call audio signal is transmitted to the digital pillow speaker. A digital microphone signal is received 109 from the digital pillow speaker. The received 109 digital nurse call signal is transmitted 112 as an analog microphone signal on the nurse call audio port. The method 100 may further comprise conditioning 115 the analog microphone signal to match a microphone signal expected by a nurse call system. For example, the analog microphone signal may be conditioned 115 by attenuating the signal.

Figure 5:
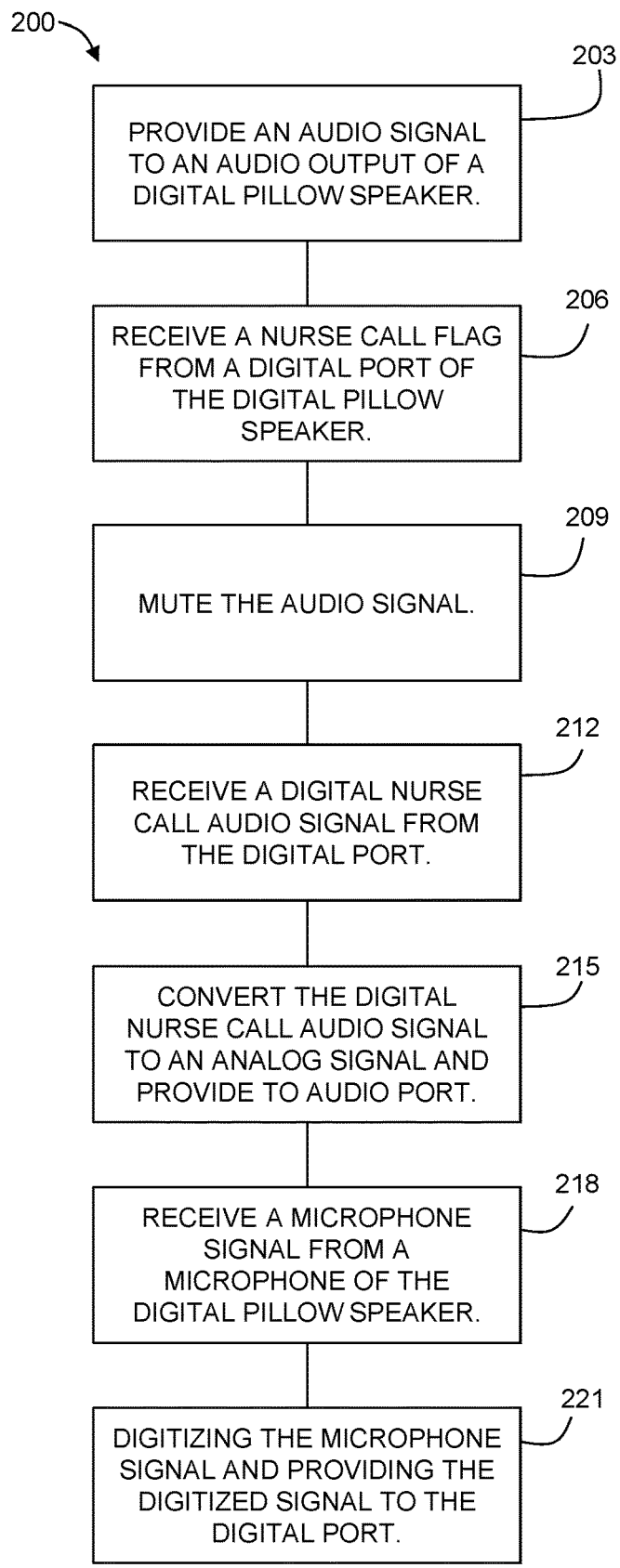
FIG. 5 is a method according to another embodiment of the present disclosure.

With reference to FIG. 5, in another aspect, the present disclosure may be embodied as a method 200 for prioritizing audio signals in a digital pillow speaker. Such a method 200 may be performed by, for example, a PID of a pillow speaker system similar to that described above. Other pillow speaker systems may perform method 200 by way of one or more other components. The method 200 comprises providing 203 an audio signal to an audio output of the digital pillow speaker. A nurse call indicator is received 206 from a digital port of the digital pillow speaker. The method 200 comprises muting 209 the audio signal provided 203 to the audio output of the digital pillow speaker. A digital nurse call audio signal is received 212 from the digital port. The received 212 digital nurse call audio signal is converted to an analog nurse call audio signal and the analog nurse call audio signal is provided to the audio output. The method 200 may further comprise receiving 215 a microphone signal from a microphone of the digital pillow speaker. The received 215 microphone signal is digitized 218 and the resulting digital microphone signal is provided 221 to the digital port.

Figure 6:
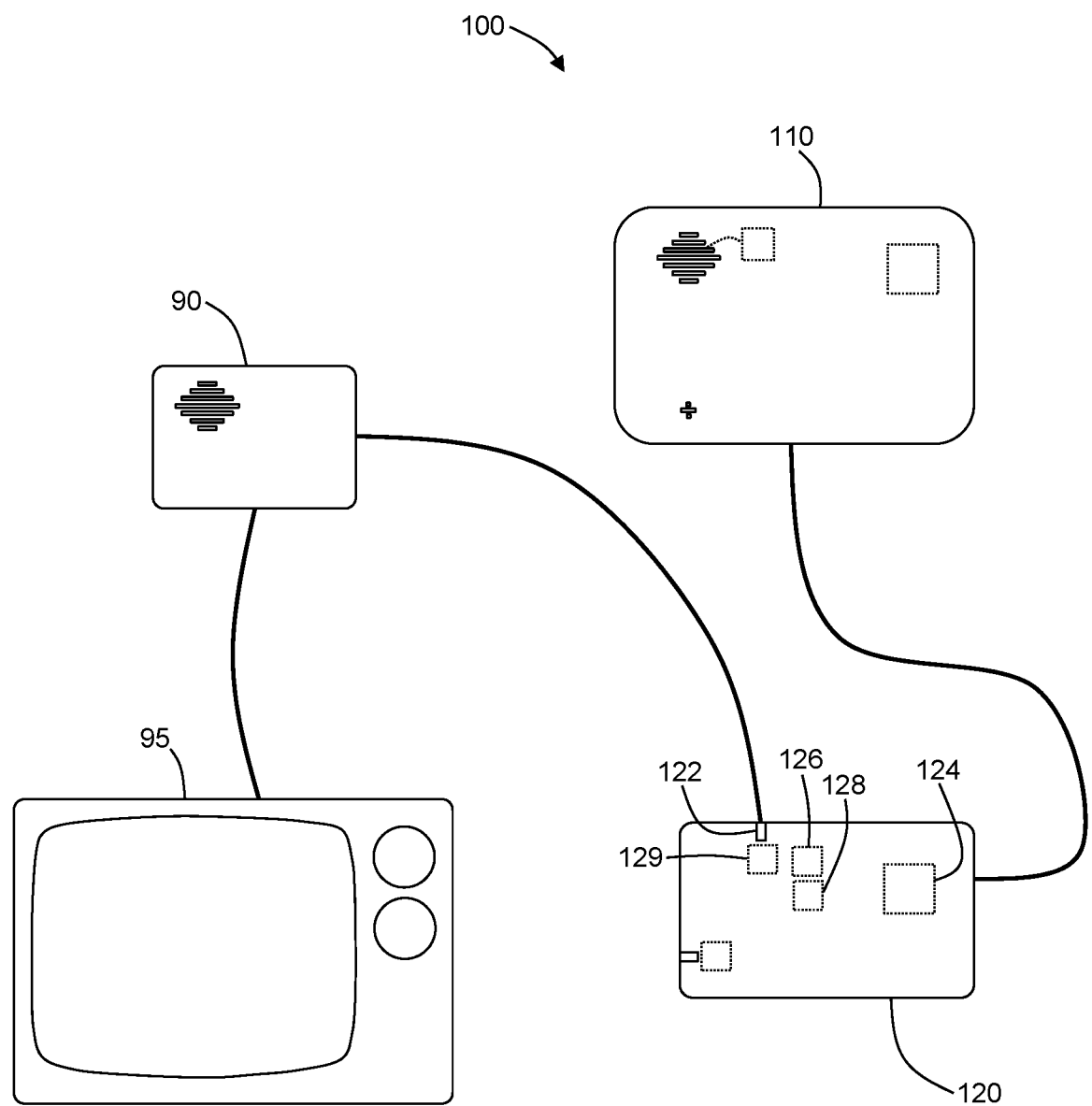
FIG. 6 is a diagram of a pillow speaker system according to another embodiment of the present disclosure.

In another aspect, a pillow speaker system 100 receives a signal at an audio port, for example, the nurse call audio port 122, which could be entertainment audio, nurse call audio, or otherwise. For example, FIG. 6 depicts a pillow speaker system 100 with a PID 110 in communication with a hub 120. The hub 120 has a nurse call audio port 122 to which a nurse station 90 has been connected. An entertainment device, for example, TV 95, is connected to the nurse station 90, such that an audio signal from the entertainment device 90 is transmitted to the hub 120 by way of the nurse station 90. As such, the nurse call audio port 122 receives a signal that may be a nurse call audio signal or an entertainment audio signal. In such an embodiment, detection circuit 124 is configured to distinguish between a nurse call audio signal and an entertainment audio signal—i.e., to identify a nurse call audio signal.

The present disclosure may be embodied as a method for identifying a nurse call audio signal on an audio line, for example, an audio line connected to nurse call audio port. The method comprises detecting a first audio source transition. Once a first audio source transition is detected, a subsequent audio signal is identified as a nurse call audio signal. Similarly, a second audio source transition may be detected, and a subsequent audio signal may be identified as an entertainment audio signal. The first and/or second audio source transitions may be detected in various ways, several examples below are provided below and described in terms of detecting a first audio source transition. It should be noted that the techniques may equally apply to detecting a second audio source transition.

In a first example, a momentary audible tone may be detected. For example, a patient may be watching TV, such that the audio line transmits an entertainment audio signal from the TV. The nurse call station 90 may sound an audible tone (e.g., a beep, a buzz, a ring, etc.) when a nurse call signal is incoming. This audible tone may be detected using, for example, a microphone 118 of the pillow speaker system 100. The audible tone may be pre-determined to be a tone that is distinguishable from other sounds expected in a typical room. For example, the tone may have a particular frequency (or frequencies), pattern, volume, etc. In another example, the first audio source transition may be detected by detecting an electrical signal corresponding to a pre-determined tone. For example, a pre-determined tone signal may be transmitted on the audio line (or a separate line) and the pillow speaker system may include a tone detection circuit to detect the electrical signal.

In another example, a discontinuity on the audio line may indicate the first audio source transition. For example, an entertainment audio signal may have characteristics such as an threshold amplitude that the entertainment signal always exceeds, or a characteristic background signal that is always present (one or more frequencies that are present in the background signal). When a nurse call audio signal is broadcast on the audio line, a discontinuity may be detected where, for example, the characteristics of the entertainment audio signal are no longer present, or additional characteristic signals are added. Such discontinuities may be detected by the pillow speaker system and used to detect the first audio source transition. In a particular example of a discontinuity, the audio signal may include a "switch bounce" at the time of the first audio source transition. Such a switch bounce may occur, for example, where the nurse has depressed a button in order to transmit the nurse call audio (e.g., a microphone switch/button is depressed while a nurse talks into the microphone at a nurse station).

Figure 8:
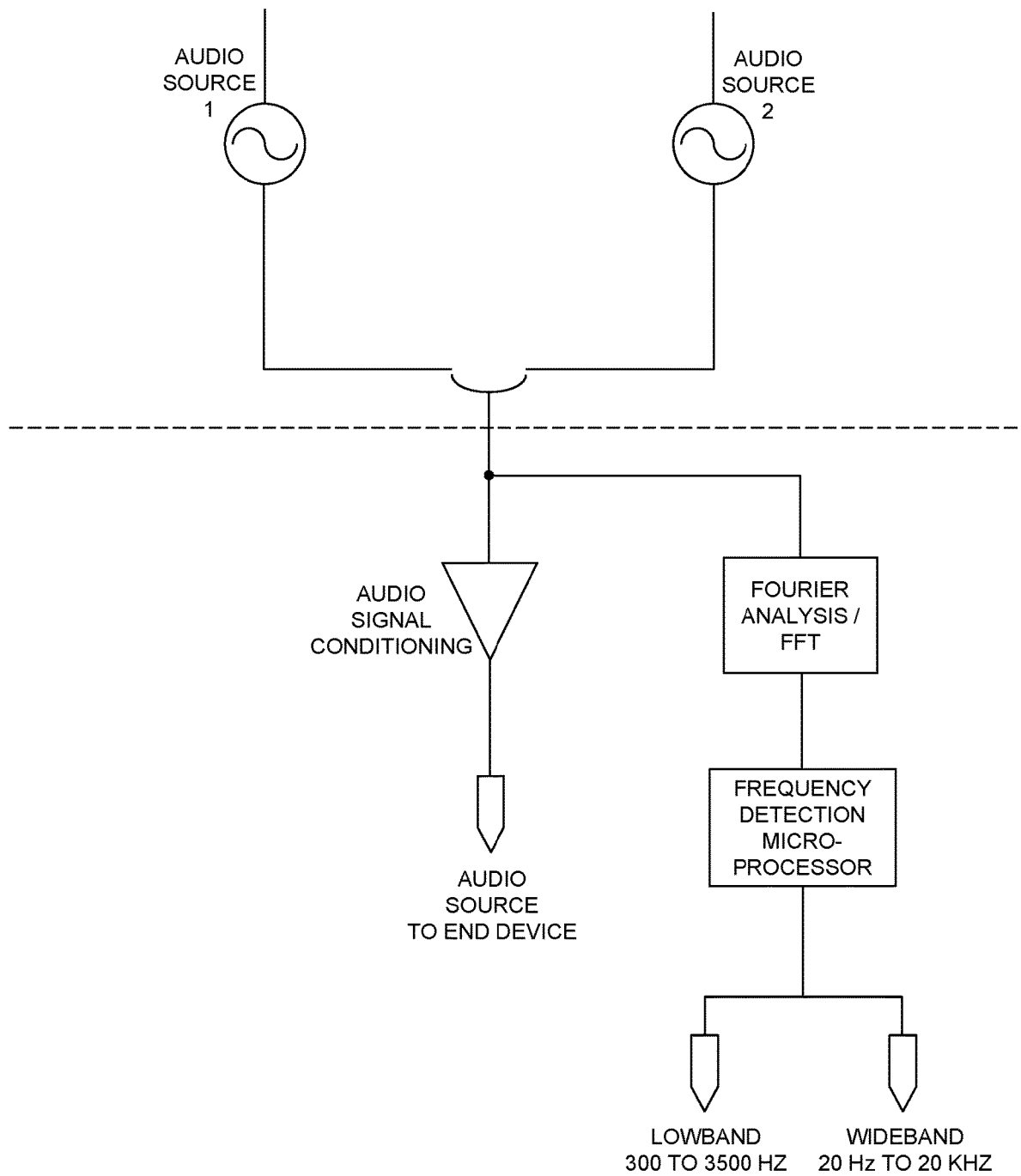
FIG. 8 is a diagram of audio detection according to another embodiment of the present disclosure.

In another example (see FIG. 8), a change in the bandwidth in use by the audio signal may indicate a first audio source transition. For example, an entertainment audio source, such as a television, may have an audio signal which occupies a frequency range between 20 Hz to 20,000 Hz (for example, similar to a typical human audible range, etc.), while a nurse call audio signal transmitted by a nurse station may occupy a narrower frequency range of between 300 Hz to 3500 Hz (for example, similar to a typical telephony range). The pillow speaker system may be configured to detect a change in the bandwidth of a received audio signal as a first audio source transition from an entertainment audio signal to a nurse call audio signal. For example, the pillow speaker system may include a circuit to sample the signal and conduct a Fourier analysis (using, for example, Fast-Fourier Transform (FFT) or other technique). As such, the frequency domain signal may be sampled for the presence of frequency components above and/or below a threshold frequency. The threshold frequency may be predetermined as a frequency which reliably distinguishes between the expected wide-bandwidth entertainment audio signal and the expected low-bandwidth nurse call signal. In the example frequencies noted above, the threshold frequency may be selected as 3500 Hz. Other frequencies may be used according to the design parameters for a particular application. A frequency detection circuit (for example, a microprocessor) may be configured to detect the presence of "low" versus "wide" frequency components and provide a differentiated digital output accordingly. In some cases, a wide-band system may have only low band components at any given time. The noise floor of the audio source transfer function may be sufficient audio presence for discerning between audio sources. In some embodiments, the frequency components are analyzed along with the corresponding amplitudes of the frequency components in order to more effectively discern between audio sources.

Figure 7:
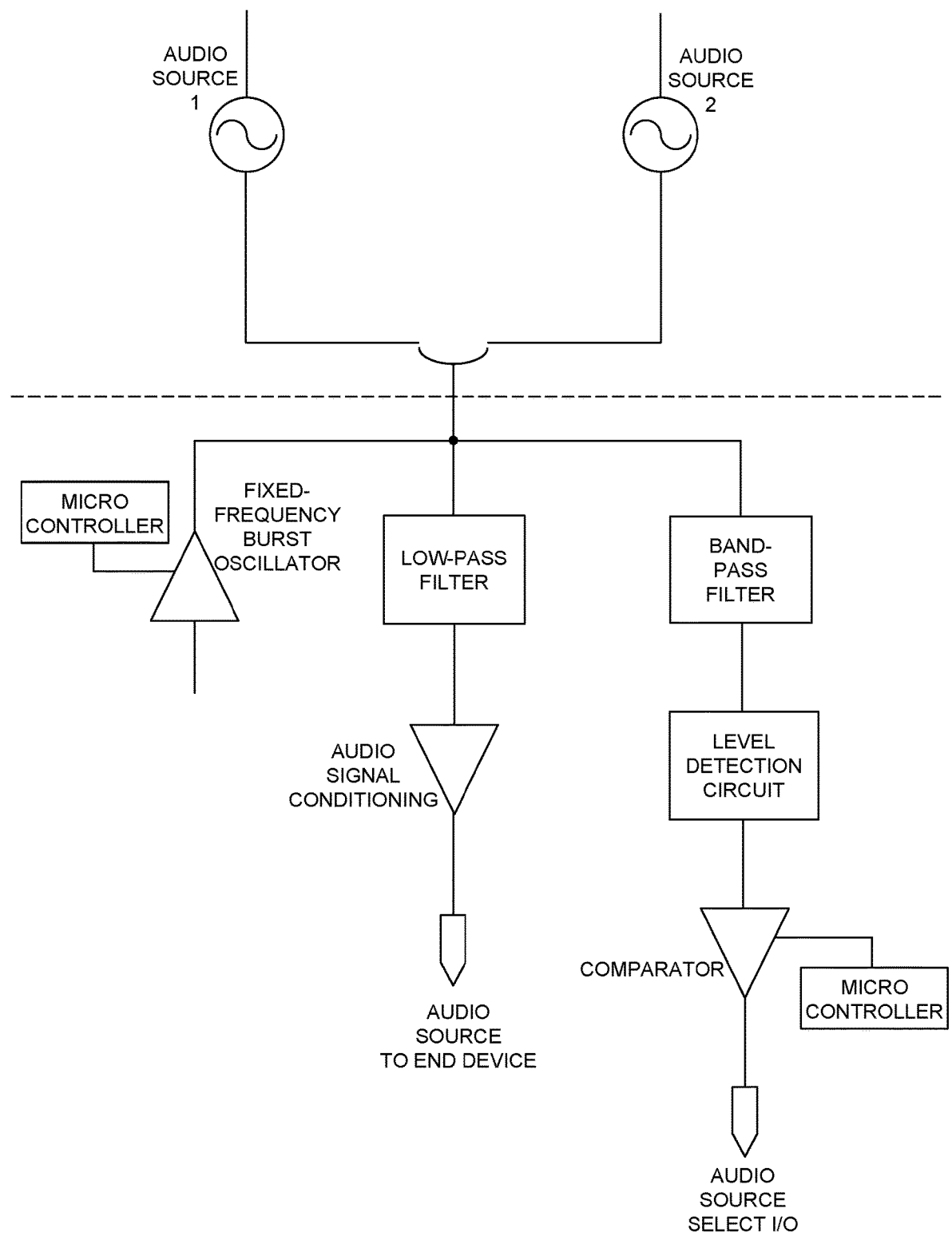
FIG. 7 is a diagram of audio detection according to an embodiment of the present disclosure.

In another example (see FIG. 7), an out-of-frequency band reflection may be detected to indicate a first audio source transition. For example, the pillow speaker system may generate a high-frequency signal on the audio line. By high-frequency, it is meant that the frequency is above that of the expected audio signals on the line (for example, greater than 20,000 Hz—i.e., out-of-band) and at a frequency where the audio line acts as a transmission line. The high-frequency signal is reflected due to the high impedance at the output of the current source of audio, for example, a TV. The reflected signal is detected and the characteristics of the reflected signal are determined to be consistent with a signal reflected due to the output impedance of the audio source (e.g., determined to be the TV). This process is repeated periodically. When the audio source changes due to a nurse call, the reflected signal has different characteristics due to the inherent differences in the output impedance of the nurse call station. As such, the reflected signal is detected and the impedance characteristics are determined to be consistent with that of the nurse call audio source. It should be noted that it may be advantageous to characterize reflected signals on setup of a pillow speaker system. In this way, the reflected signals of the various audio sources (each having an output impedance which is different from the others) will be known such that the audio source may be properly identified. In an exemplary system, a fixed-frequency burst oscillator (FFBO) is used to generate a periodic high frequency signal at a predetermined duration and interval. In some embodiments, a low-pass filter prevents the reflected signal from passing through to the end device. A reflected-signal processing circuit may include a band-pass filter, a level detection circuit, and/or a comparator to characterize the reflected signal.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

We claim:

1. A pillow speaker system, comprising:
   a patient interface device (PID) having a processor and an audio output, the PID being capable of generating audio;
   a hub in communication with the PID, the hub comprising:
      a nurse call audio port to communicate with a nurse call station;
      a detection circuit to detect a nurse call signal received on the nurse call audio port and to provide a nurse call indicator to the PID if a nurse call signal is present; and
   wherein the processor of the PID is programmed to:
      receive the nurse call indicator from the detection circuit of the hub;
      provide a nurse call audio signal to the audio output if the nurse call indicator is received; and
      mute audio signals to the audio output except the nurse call audio signal.

2. The pillow speaker system of claim 1, wherein the detection circuit detects a nurse call signal by detecting an audio signal on the nurse call audio port.

3. The pillow speaker system of claim 1, wherein the detection circuit detects a nurse call signal by detecting a nurse call indicator signal.

4. The pillow speaker system of claim 1, wherein the hub in digital communication with the PID, wherein the nurse call audio port is in analog communication with the hub, and the hub digitizes the nurse call audio signal to send a digital nurse call audio signal to the PID.

5. The pillow speaker system of claim 4, wherein the nurse call indicator is a digital signal.

6. The pillow speaker system of claim 1, wherein the PID has a microphone and the processor is further programmed to provide a microphone signal from the microphone to the nurse call audio port if a nurse call indicator is received.

7. The pillow speaker system of claim 6, further comprising a conditioner for conditioning the microphone signal.

8. The pillow speaker system of claim 7, wherein the conditioner is an attenuator.

9. The pillow speaker system of claim 7, wherein the conditioner is a software module programmed in the processor.

10. The pillow speaker system of claim 7, wherein the conditioner is a discrete electrical circuit.

11. The pillow speaker system of claim 4, further comprising an entertainment audio port in analog communication with the hub, and the hub digitizes an entertainment audio signal of the entertainment audio line to send a digital entertainment audio signal to the PID.

12. The pillow speaker system of claim 4, further comprising an isolation network in communication with the nurse audio port.

13. The pillow speaker system of claim 12, further comprising an impedance-matching network.

14. The pillow speaker system of claim 1, wherein the processor is further programmed to unmute other signals when the nurse call indicator is de-asserted.

15. The pillow speaker system of claim 1, wherein the detection circuit de-assert the nurse call indicator if a nurse call signal is not detected for a predetermined period of time.

16. The pillow speaker system of claim 1, wherein the detection circuit comprises an envelope detector.

17. The pillow speaker system of claim 16, wherein the detection circuit further comprises a comparator.

18. A method of providing a nurse call audio signal to a pillow speaker, comprising:
   providing a pillow speaker having a patient interface device (PID) and a pillow speaker hub,
      wherein the pillow speaker hub is in communication with a nurse call system, and
      wherein the pillow speaker hub is further in communication with the PID;
   detecting, at the pillow speaker hub, a nurse call signal from the nurse call system, and asserting a nurse call indicator for the pillow speaker if a nurse call signal is detected;
   digitizing a nurse call audio signal received at a nurse call audio port of the pillow speaker hub and transmitting the digitized nurse call audio signal to the PID;
   receiving a digital nurse call microphone signal from the PID; and
   transmitting the digital nurse call microphone signal to the nurse call system as an analog microphone signal on the nurse call audio port.

19. The method of claim 18, further comprising conditioning the analog microphone signal for use with a nurse call system.

20. A method of prioritizing audio signals in a pillow speaker, comprising:
   providing an audio signal to an audio output of the pillow speaker;
   receiving a nurse call indicator from a digital port of the pillow speaker;
   muting the audio signal;
   receiving a digital nurse call audio signal from the digital port;
   converting the digital nurse call audio signal to an analog nurse call audio signal and providing the analog nurse call audio signal to an audio output.

21. The method of claim 20, further comprising:
   receiving a microphone signal from a microphone of the digital pillow speaker; and
   digitizing the microphone signal to provide a digital microphone signal to the digital port.

22. A method for identifying a nurse call audio signal on an audio line, comprising:
   detecting a first audio source transition on the audio line; and
   identifying an audio signal on the audio line and subsequent to the first audio source transition as a nurse call audio signal.

23. The method of claim 22, further comprising:
   detecting a second audio source transition; and
   identifying an audio signal subsequent to the second audio source transition as an entertainment audio signal.

24. The method of claim 22, wherein the first audio source transition is detected by detecting, using a pillow speaker microphone, an audible tone.

25. The method of claim 22, wherein the first audio source transition is detected by detecting, using a tone detection circuit, an electrical signal corresponding to a pre-determined tone.

26. The method of claim 22, wherein the first audio source transition is detected by detecting a discontinuity on the audio line.

27. The method of claim 26, wherein the electrical signal discontinuity is a switch bounce, electrical spike, or voltage transition.

28. The method of claim 22, wherein the audio source transition is detected by detecting a change in bandwidth on the audio line.

29. The method of claim 22, wherein the audio source transition is detected by detecting a change in an out-of-frequency band reflection on the audio line.

30. The method of claim 22, wherein the audio source transition is detected by detecting a change in voltage level on the audio line.

\* \* \* \* \*